US011478131B2

(12) United States Patent
Chelala et al.

(10) Patent No.: US 11,478,131 B2
(45) Date of Patent: Oct. 25, 2022

(54) DEVICES, SYSTEMS AND METHODS FOR TRANSMITTING MOTION TO THE DISTAL TIP OF AN ENDOSCOPIC ACCESSORY TOOL

(71) Applicants: Boston Scientific Scimed, Inc., Maple Grove, MN (US); The Johns Hopkins University, Baltimore, MD (US)

(72) Inventors: Marc Chelala, Baltimore, MD (US); Sritam P. Rout, Lowell, MA (US); Maria F. Torres, Baltimore, MD (US); Kyle R. Cowdrick, Baltimore, MD (US); David M. Gullotti, Baltimore, MD (US); Amir Hossein Soltanianzadeh, Baltimore, MD (US); George Coles, Baltimore, MD (US); Youseph Yazdi, Ellicott City, MD (US); Pankaj J. Pasricha, Ellicott City, MD (US); Ryan V. Wales, Northborough, MA (US); Demetri Monovoukas, Cambridge, MA (US); John T. Favreau, Spencer, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 790 days.

(21) Appl. No.: 16/242,416

(22) Filed: Jan. 8, 2019

(65) Prior Publication Data
US 2019/0208990 A1 Jul. 11, 2019

Related U.S. Application Data

(60) Provisional application No. 62/615,109, filed on Jan. 9, 2018.

(51) Int. Cl.
*A61B 1/01* (2006.01)
*A61B 1/00* (2006.01)
(Continued)

(52) U.S. Cl.
CPC ........ *A61B 1/00133* (2013.01); *A61B 1/0016* (2013.01); *A61B 1/0051* (2013.01);
(Continued)

(58) Field of Classification Search
CPC .... A61B 17/320068; A61B 17/320092; A61B 2017/320072; A61B 2017/003; A61B 1/01; A61B 1/005; A61B 1/018; A61B 1/0057
See application file for complete search history.

(56) References Cited

U.S. PATENT DOCUMENTS

| 6,379,319 B1 * | 4/2002 | Garibotto | A61B 17/11 600/585 |
| 2010/0217151 A1 * | 8/2010 | Gostout | A61B 10/02 600/565 |

OTHER PUBLICATIONS

Abdomen anatomy regions 'liver stomach removed'—Google Search. Available at: https://s-media-cache-ak0.pinimg.com/originals/8f/ee/22/8fee229d525b87262ebe19fb16d85437.png. (Accessed: Oct. 9, 2016).

(Continued)

*Primary Examiner* — Vi X Nguyen
(74) *Attorney, Agent, or Firm* — Seager, Tufte & Wickhem, LLP (57) ABSTRACT

The present disclosure relates generally to the field of medical devices and establishing access to body passageways. In particular, the present disclosure relates to devices, systems and methods to facilitate entry of an endoscopic accessory tool into and/or through patient-specific anatomies. For example, the devices, systems and methods of the present disclosure may transmit mechanical motion to the distal end of an endoscopic accessory tool to facilitate atraumatic access to tortuous or otherwise restricted anatomies.

18 Claims, 11 Drawing Sheets

(51) Int. Cl.
*A61B 1/005* (2006.01)
*A61M 25/01* (2006.01)
*A61M 25/09* (2006.01)
*A61B 17/00* (2006.01)
*A61B 17/34* (2006.01)
*A61B 17/32* (2006.01)
*A61B 18/00* (2006.01)

(52) U.S. Cl.
CPC ........... *A61B 1/01* (2013.01); *A61M 25/0133* (2013.01); *A61M 25/09041* (2013.01); *A61B 1/00087* (2013.01); *A61B 17/3415* (2013.01); *A61B 2017/003* (2013.01); *A61B 2017/00296* (2013.01); *A61B 2017/00367* (2013.01); *A61B 2017/00818* (2013.01); *A61B 2017/320095* (2017.08); *A61B 2018/00595* (2013.01); *A61B 2018/00601* (2013.01)

(56) References Cited

OTHER PUBLICATIONS

UpToDate: Endoscopic retrograde cholangiopancreatography: Indications, patient preparation, and complications. Available at: http://www.uptodate.com/contents/endoscopic-retrograde-cholangiopancreatography-indications-patient-preparation-and-complications (Accessed: Oct. 9, 2016).

Adler, D. G. et al. ASGE guideline: the role of ERCP in diseases of the biliary tract and the pancreas. Gastrointest. Endosc. 62, 1-8 (2005).

"BBC—GCSE Bitesize: Types of Motion." Retrieved from Web. Apr. 4, 2017. http://www.bbc.co.uk/schools/gcsebitesize/design/systemscontrol/mechanismsrev8.shtml.

* cited by examiner

DEVICES, SYSTEMS AND METHODS FOR TRANSMITTING MOTION TO THE DISTAL TIP OF AN ENDOSCOPIC ACCESSORY TOOL

CROSS REFERENCE TO RELATED APPLICATIONS

This application claims the benefit of priority under 35 U.S.C. § 119 to U.S. Provisional Patent Application Ser. No. 62/615,109, filed on Jan. 9, 2018, which is incorporated by reference in its entirety for all purposes.

FIELD

The present disclosure relates generally to the field of medical devices and establishing access to body passageways. In particular, the present disclosure relates to devices, systems and methods to facilitate entry of an endoscopic accessory tool into and/or through patient-specific anatomies.

BACKGROUND

Medical professionals face a variety of technical challenges when performing endoscopic cannulation procedures that require advancing a guidewire and/or endoscopic accessory tool (e.g., sphincterotome, cannula, catheter, etc.) into and through challenging patient anatomies. For example, a target body passageway may be oriented at a difficult angle relative to the endoscopic accessory tool, have a very small or sealed opening, or include a tortuous anatomy, blockages (e.g., stones, etc.) and benign or malignant structures. To facilitate smooth and efficient entry of a guidewire and endoscopic accessory tool into/through a target body passageway, medical professionals often manually rotate, oscillate, linearly advance and/or reciprocate the endoscopic accessory tool, and by proxy the guidewire itself, to "wiggle" the guidewire and endoscopic accessory tool and thereby reduce friction exerted against the opening and/or inner wall of the passageway. As might be expected, precise control of the force and frequency of movement imparted to the accessory tool and guidewire largely remains crude and uncontrolled. Even experienced medical professionals often require multiple attempts to achieve successful cannulation, especially when working against the natural friction and abnormal patient-specific pathologies of the specific body passageway. Naturally, the likelihood of causing trauma to the tissues comprising or surrounding the target body passageway increases with the number of cannulation attempts. In some instances, the medical professional may be required to abort the cannulation procedure entirely. In other instances, the traumatized tissues may be prone to harmful and potentially life-threatening post-operative inflammation.

A variety of advantageous medical outcomes may be realized by the devices, systems and methods of the present disclosure which facilitate enhanced entry of a guidewire and endoscopic accessory tool into and/or through challenging patient-specific anatomies.

SUMMARY

In one aspect, the present disclosure relates to a medical device comprising an elongate tubular body having a proximal end, a distal end and a length therebetween. The elongate tubular body may include a first lumen extending between the proximal and distal end. A distal portion of the elongate tubular body may include an opening in communication with the first lumen. An elevator may be disposed at a first location within the distal portion of the elongate tubular body. The elevator may be configured to move between a first position and a second position relative to a longitudinal axis of the elongate tubular body. An actuator may be disposed at a second location within the distal portion of the elongate tubular body. The second location may be adjacent to the first location such that the actuator may be configured to transmit mechanical motion to the elevator. The second location may be on one side of the first lumen proximal to the elevator. Alternatively, the second location may be on opposite sides of the first lumen proximal to the elevator. The elongate tubular body may further include a second lumen adjacent to first lumen. The first lumen may be configured to receive an endoscopic accessory tool therethrough. The elevator may be configured to act upon a distal portion of the endoscopic accessory tool as the elevator moves between the first and second positions. The actuator may be configured to transfer mechanical motion to the distal portion of the endoscopic accessory tool.

In another aspect, the present disclosure relates to a medical device comprising an elongate tubular body having a proximal end, a distal end, and a length therebetween. The elongate tubular body may include a first lumen extending between the proximal and distal ends. A distal portion of the elongate tubular body may include an opening in communication with the first lumen. An elevator may be disposed at a first location within a distal portion of the elongate tubular body. The elevator may be configured to move between a first position and a second position relative to a longitudinal axis of the elongate tubular body. An endcap may be disposed around the distal portion of the elongate tubular body. The endcap may include an opening configured to align with the opening of the elongate tubular body. An actuator may be disposed within the endcap adjacent to the opening of the endcap. The actuator may be configured to transmit mechanical motion across the opening of the endcap. The first lumen may be configured to receive an endoscopic accessory tool therethrough. The elevator may be configured to act upon a distal portion of the endoscopic accessory tool as the elevator moves between the first and second positions. The actuator may be configured to transmit mechanical motion to a portion of the endoscopic accessory tool extending through the opening of the endcap.

In yet another aspect, the present disclosure relates to an endoscopic accessory tool comprising an elongate member having a proximal portion with a proximal end, a distal portion with a distal end and a lumen extending therebetween. The distal portion of the elongate member may be configured to receive energy propagated along a length of the elongate member to transmit motion to the distal portion of the elongate member. The motion may be transmitted in a plurality of directions relative to a longitudinal axis of the elongate member. The lumen may be configured to receive a guidewire therethrough. An actuator may be disposed on or within a portion of the elongate member. The actuator may be attached to the distal end of the elongate member. The actuator may be disposed within the proximal portion of the elongate member. The energy may include vibrational energy, and the actuator may propagate the vibrational energy along the length of the elongate member to transmit mechanical motion to the distal portion of the elongate member. A cutting wire may extend along the length of the elongate member. A proximal end of the cutting wire may be connected to an energy source. The energy source may be configured to deliver cauterizing energy to a distal portion of the cutting wire. A portion of an inner surface of the elongate member may include a surface feature configured to slidably engage a corresponding surface feature on an outer surface of the guidewire. The surface features may be disposed on the proximal portion of the elongate member and a proximal portion of the guidewire. The surface features may be disposed on the distal portion of the elongate member and a distal portion of the guidewire. The surface feature of the guidewire may extend around a full circumference of the guidewire. The surface feature of the guidewire may extend around less than a full circumference of the guidewire. The elongate member may be configured to extend through a medical device. The medical device may include an elongate tubular body having a proximal end, a distal end and a length therebetween. The elongate tubular body may include a first lumen extending between the proximal and distal ends. A distal portion of the elongate tubular body may include an opening in communication with the first lumen. An elevator may be disposed at a first location within the distal portion of the elongate tubular body. The elevator may be configured to move between a first position and a second position relative to a longitudinal axis of the elongate tubular body. An actuator may be disposed at a second location within the distal portion of the elongate tubular body. The actuator of the medical device may be configured to transfer mechanical motion to the distal portion of the endoscopic accessory tool. In various embodiments, the actuator of the medical device may be configured to transfer mechanical motion to the distal portion of the endoscopic accessory tool in addition to, or as an alternative to, the actuator disposed on or within a portion of the elongate member.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to medical devices and systems (e.g., endoscopic accessory tools and/or guidewires inserted through a duodenoscope, etc.) for selective cannulation of the common bile duct (CBD) or pancreatic duct (PD) during an Endoscopic Retrograde Cholangiopancreatography (ECRP) procedure, it should be appreciated that such medical devices and systems may be used in a variety of medical procedures which require navigating one or more accessory tools through ductal, luminal, or vascular anatomies, including, for example, interventional radiology procedures, balloon angioplasty procedures, thrombolysis procedures, angiography procedures and the like. The disclosed medical devices and systems may be inserted via different access points and approaches, e.g., percutaneously, endoscopically, laparoscopically or some combination thereof.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

Figure 1:
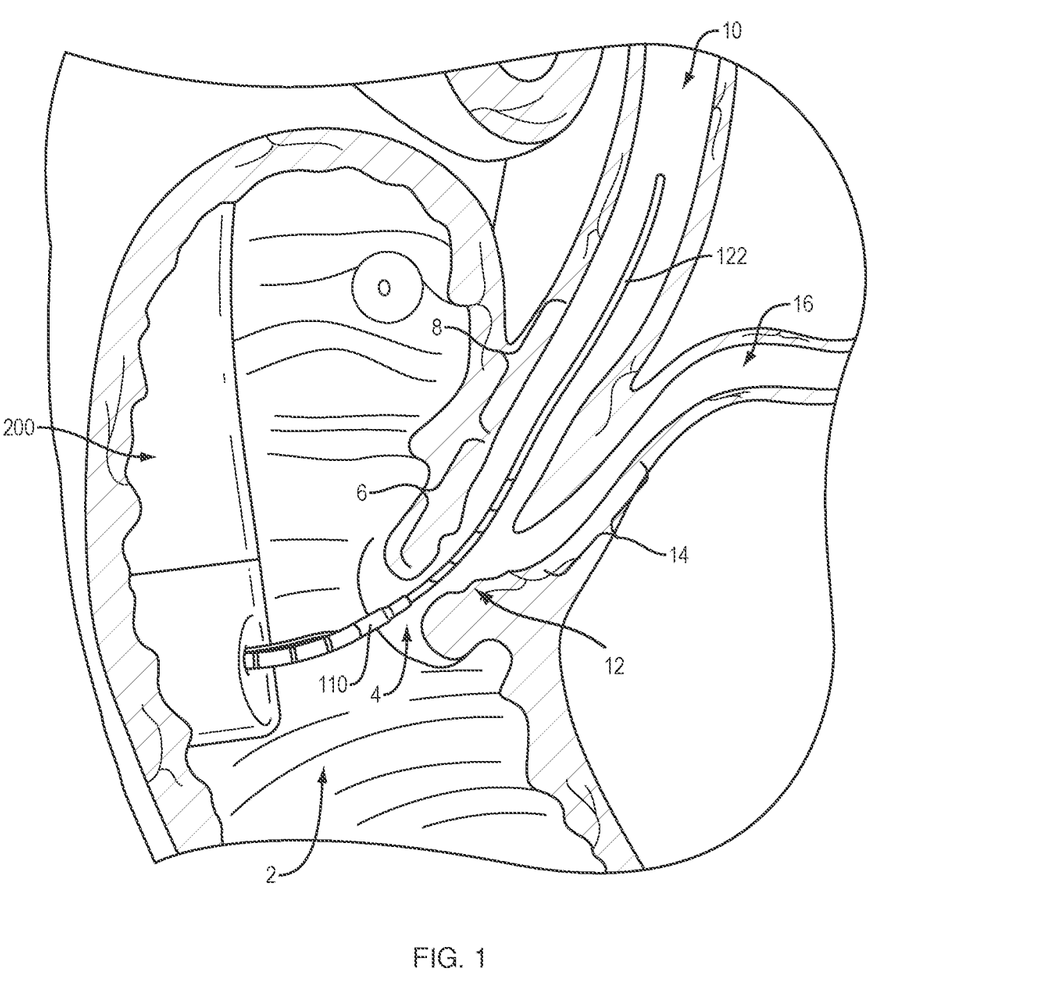
FIG. 1 provides a schematic illustration of a medical device disposed within a body passageway of a patient, according to one embodiment of the present disclosure.

Selective cannulation refers to the act of passing a guidewire and endoscopic accessory tool through the major papilla 4 (e.g., ampullary entry) near the descending duodenum 2 to access the Sphincter of Oddi Complex, which is defined by the intersection of the Sphincter Papillae 12, Sphincter Ampullae 6 and Sphincter Pancreaticus 14. For example, referring to FIG. 1, a distal portion of a medical device 200 (e.g., duodenoscope) may be positioned within the descending duodenum, and a guidewire 122 and elongate member 110 advanced through a working channel of the duodenoscope into the major papilla 4 and through the Sphincter Papillae 12, Sphincter Ampullae 6 and Sphincter Choledochus 8 to access the CBD 10. Alternatively, the guidewire and endoscopic accessory tool may be advanced through the major papilla 4 and through the Sphincter Papillae 12 and Sphincter Pancreaticus 14 to access the PD 16. The step of accessing the Sphincter Papillae is notoriously difficult because the opening to the major papilla is extremely small, or even completely collapsed/closed, and extends into the descending duodenum at an angle that is difficult to visualize. Thus, the medical professional is required to manipulate the endoscopic accessory tool and guidewire by manually rotating the duodenoscope and/or using an elevator within the distal head of the duodenoscope. Difficult cannulation procedures in which the medical professional fails to access the Sphincter Papillae within a certain time limit, or after a certain number of unsuccessful attempts, may lead to significant post-procedure complications, such as post-ECRP pancreatitis (PEP).

In various embodiments, the present disclosure relates to medical devices, systems and methods for selective cannulation of the common CBP or PD to treat a variety of hepatobiliary indications during an ECRP procedure. Atraumatic entry of the guidewire and endoscopic accessory tool into the luminal structures of the hepatobiliary system may be achieved through controlled reduction of friction by transmitting mechanical motion to the distal end of an endoscopic accessory tool, and by proxy the guidewire itself.

In embodiments, devices, systems, and methods may transmit motion to the distal tip of an endoscope assembly as described herein and in co-pending application filed concurrently, entitled "Medical Devices, Systems and Methods with Tip Deflection" to Reid et al., which is herein incorporated by reference in its entirety.

Figure 2A:
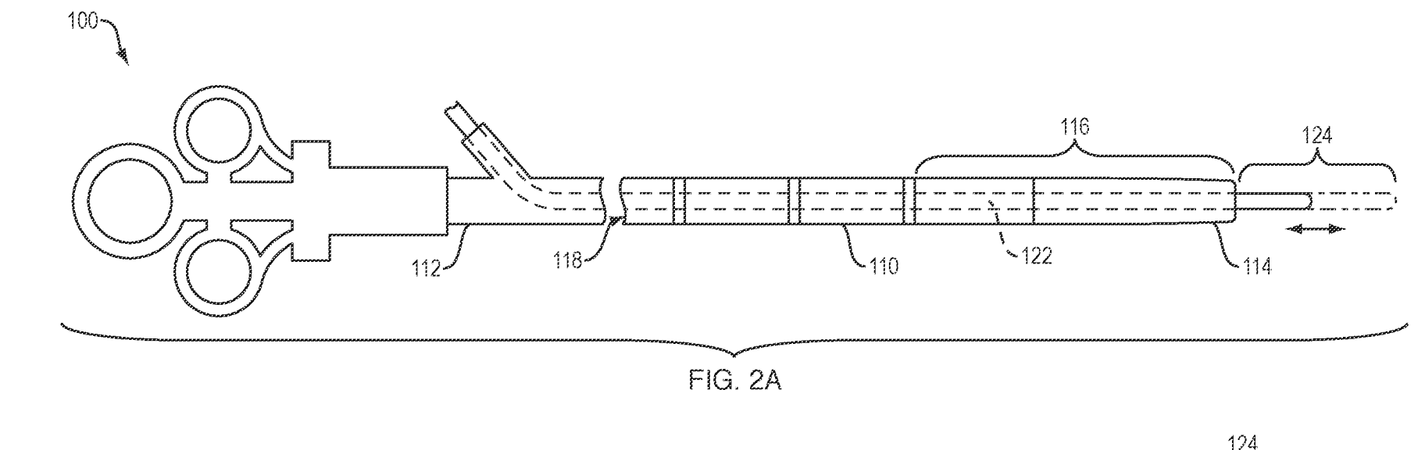
FIGS. 2A-2C provide perspective views of a distal portion of an endoscopic accessory tool, according to one embodiment of the present disclosure.
Figure 2B:
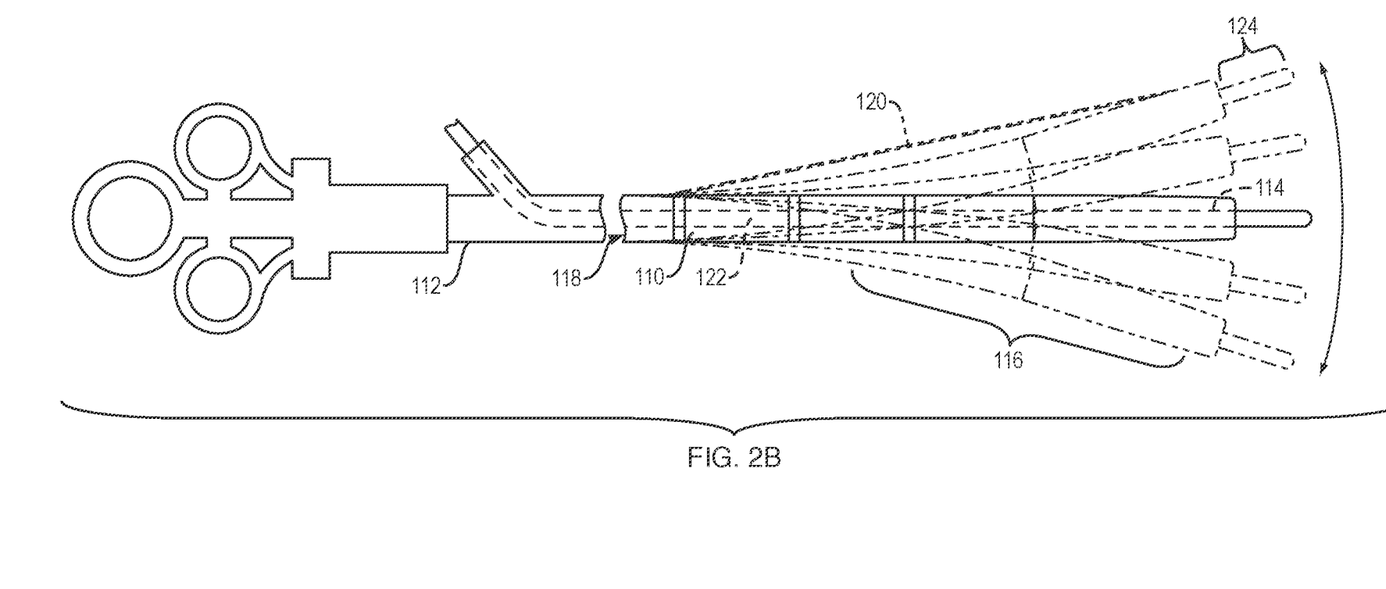
Figure 2C:
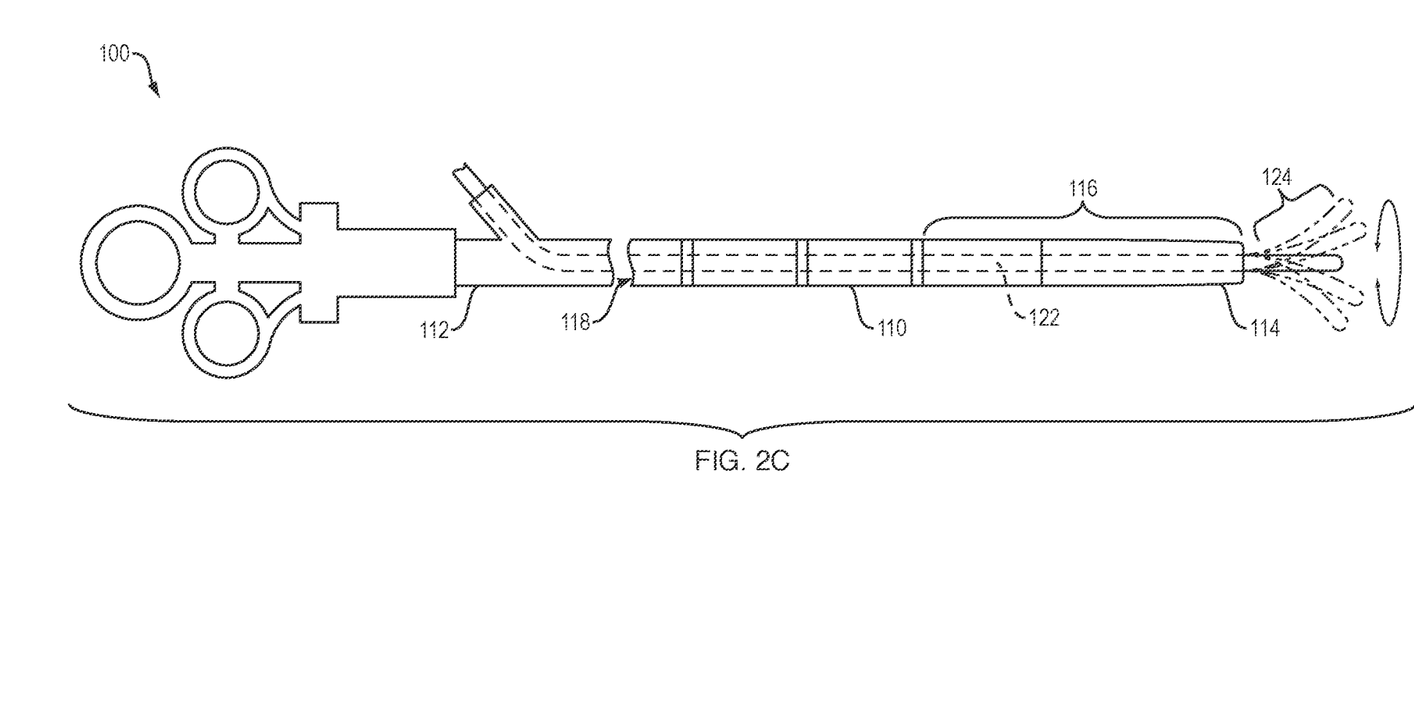

Referring to FIGS. 2A-2C, in one embodiment, an endoscopic accessory tool 100 (e.g., sphincterotome, cannula, catheter, etc.) of the present disclosure may include an elongate member 110 forming a lumen 118 and comprising a proximal end 112, a distal end 114, a length and a diameter. The lumen 118 may be configured to receive a guidewire 122 such that a distal portion 124 of the guidewire 122 extends distally beyond the distal end 114 of the elongate member 110. The elongate member 110 may include a flexible distal portion 116 configured to move (e.g., flex, bend, rotate, wobble, spin, etc.) in a plurality of directions (e.g., x, y and/or z directions), thereby imparting an identical or similar direction of movement to the distal portion 124 of the guidewire 122. Referring to FIG. 2A, in one embodiment, the distal portion 116 of the elongate member 110 may be configured to move in a linear motion (e.g., moving in a single direction along a straight line relative to a longitudinal axis of the elongate member 110), or in a reciprocating motion (e.g., backwards and forwards in a straight line along a longitudinal axis of the elongate member 110). Referring to FIG. 2B, in another embodiment, the distal portion 116 of the elongate member 110 may be configured to swing from side-to-side in a vibrating or oscillatory motion. Referring to FIG. 2C, in another embodiment, the distal portion 116 of the elongate member 110 may be configured to move in a rotary motion (e.g., 360 degrees of rotation around a central axis of the elongate member 110). As disclosed herein, the medical professional may toggle between any of these motions on demand across a range of frequencies, amplitudes and durations (e.g., brief or sustained pulses) to provide fine-tuned control of the distal portions 116, 124 of the elongate member 110 and guidewire 122 to facilitate enhanced access into and through patient-specific pathologies (e.g., tortuous anatomies, benign or malignant strictures, blockages due to stones, etc.) that may otherwise inhibit the physical movement of the endoscopic accessory tool into and through the CBD or PD.

As illustrated in FIG. 2B, in one embodiment, the endoscopic accessory tool 100 may further include a cutting wire 120 extending through or along a length of the elongate member 110. A distal end of the cutting wire 120 may be attached to the elongate member 110 at or near the distal end 114, and a proximal end of the cutting wire 120 may be attached to an energy source (not shown). A portion of the cutting wire 120 that is coextensive with the distal portion 116 of the elongate member 110 may be unattached and configured to extend at an outward angle relative to a longitudinal axis of the elongate member 110 as the distal portion 116 bends or flexes. With the distal portion 116 of the elongate member 110 held in a bent or flexed position, the medical professional may activate the energy source to energize the angled portion of the cutting wire 120, thereby providing cutting and cauterizing energy to enlarge an opening of the target body passageway. In various embodiments, the distal portion 116 of the elongate member 110 and/or the distal end of the cutting wire 120 may be configured to deliver real-time feedback information to a medical professional or computer processor, to manually or automatically adjust, e.g., increase or decrease, the frequency, direction and/or duration of movement of the distal portion 116 of the elongate member 110.

Although the endoscopic accessory tool 100 of the present disclosure may be used as a stand-alone device during an endoscopic procedure, in various embodiments the endoscopic accessory tool 100 may be configured to extend through the working channel of a medical device, e.g., a duodenoscope. Referring to FIGS. 3A-3D, in one embodiment, a medical device 200 of the present disclosure may include an elongate tubular body 130 forming a first lumen 138 (e.g., tool channel, accessory channel, etc.) and comprising a proximal end (not shown), distal end 132, a length and a diameter. A distal portion 136 of the elongate tubular body 130 may include an opening 134 (e.g., side-opening, etc.) in communication with the first lumen 138. An elevator 140 (e.g., elevator mechanism, ramp, lift, etc.) may be disposed at a first location within the distal portion 136 of the elongate tubular body 130 (e.g., at junction/intersection of the opening 134 and first lumen 138). The elevator 140 may be configured to move between a first (e.g., lowered, flat) position and a second (e.g., raised, angled) position relative to a longitudinal axis of the elongate tubular body 130. In one embodiment, an elevator wire 142 may extend through or along a length of the elongate tubular body 130, with a distal end 144 of the elevator wire 142 attached to the elevator 140 such that proximally retracting a proximal end (not shown) of the elevator wire 142 may move the elevator 140 from the first position to the second position, and distally advancing the elevator wire 142 may move the elevator 140 from the second position to the first position. The present disclosure is in no way limited to elevators actuated by an elevator wire, but may include a variety of actuation mechanism as are commonly known in the art, including, but not limited to wires, pulleys, pneumatic actuators, wireless or remote-control actuators, and the like.

In various embodiments, the first lumen 138 of the elongate tubular body 130 may be configured to slidably receive an endoscopic accessory tool 100 of the present disclosure. As will be understood by one of skill in the art, a medical professional may manipulate and/or control the distal portions 116, 124 of the elongate member 110 and guidewire 122 extending through the opening 134 of the medical device 200, e.g., by rotating or twisting the elongate tubular body 130, proximally retracting and/or distally extending the elongate member 110 within the first lumen 138 and/or moving the elevator 140 between the first and second positions.

One or more actuators 149 may be disposed at a second location within the distal portion 136 of the elongate tubular body 130, and configured to transmit mechanical motion to the distal portion 116 of the elongate member 110 within the distal portion 136 of the elongate tubular body 130, as discussed below.

Figure 3A:
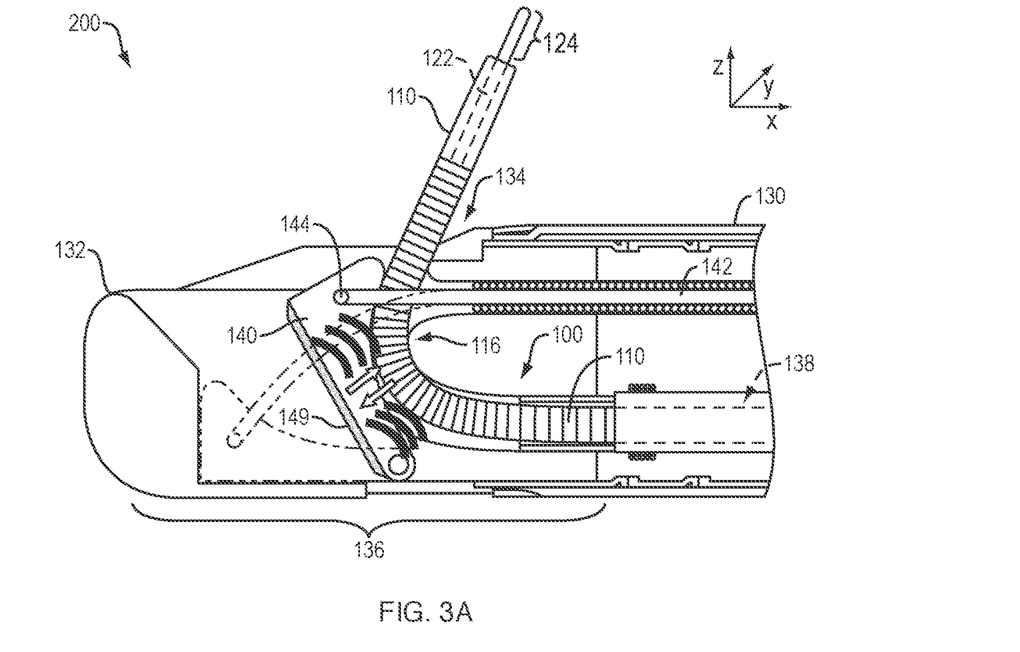
FIGS. 3A-3D provide perspective side views of a medical device and endoscopic accessory tool, according to one embodiment of the present disclosure.
Figure 3B:
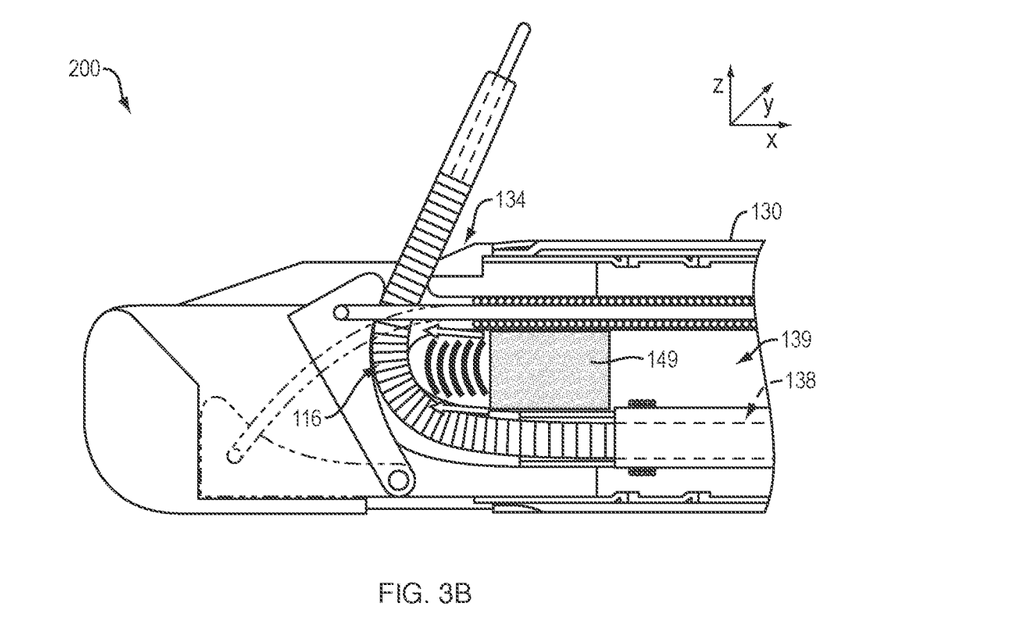

Referring to FIG. 3A, in one embodiment, the second location may be adjacent to the first location such that the actuator(s) 149 are configured to transmit mechanical motion in the −y to +y direction through the elevator 140 to the distal portion 116 of the elongate member 110 in contact with the elevator 140. For example, the actuator(s) 149 may be mounted adjacent to (e.g., in the vicinity of, below, behind, underneath, etc.) or in direct contact with a surface of the elevator 140. In addition, or alternatively, the actuator(s) 149 may be embedded on or within a portion of the elevator 140. Referring to FIG. 3B, in another embodiment, the medical device 200 may include a second lumen 139 (e.g., working channel, biopsy channel, etc.) coextensive with the first lumen 138 along the length of the elongate tubular body 130. The second location may be within or adjacent to a distal end of the second lumen 139 and proximal to the elevator 140 such that the actuator(s) 149 transmit mechanical motion in the −x to +x direction (e.g., back-and-forth) to the distal portion 116 of the elongate member 110 below the opening 134.

Figure 3C:
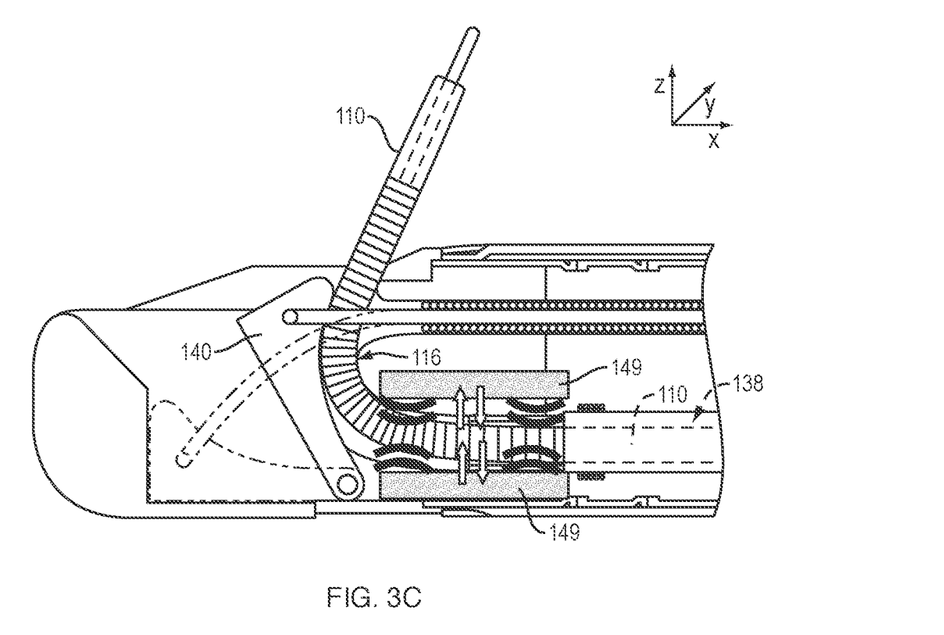
Figure 3D:
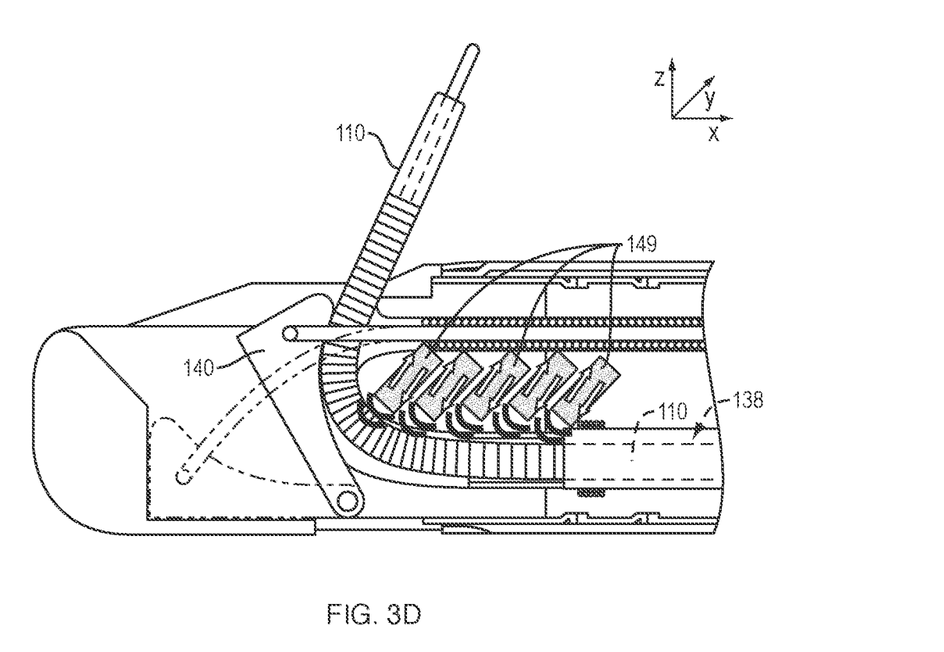

Referring to FIG. 3C, in another embodiment, the second location may be on opposite sides of the first lumen 138 such that the actuator(s) 149 transmit mechanical motion in the −z to +z direction to the elongate member 110, e.g., proximal to the elevator 140. Referring to FIG. 3D, in another embodiment, the second location may be on one side (e.g., top side) of the first lumen 138 such that the actuator(s) 149 transmit mechanical motion in the −y to +y direction, e.g., proximal to the portion of the elongate member 110 in contact with the elevator 140. The number, location, arrangement and/or orientation of actuator(s) 149 is not limited to the embodiments described herein. In various embodiments, any combination of the actuator configurations disclosed herein may be combined to transmit mechanical motion to the elongate member 110 and guidewire 122 in any of the x, y, and/or z directions.

Figure 4:
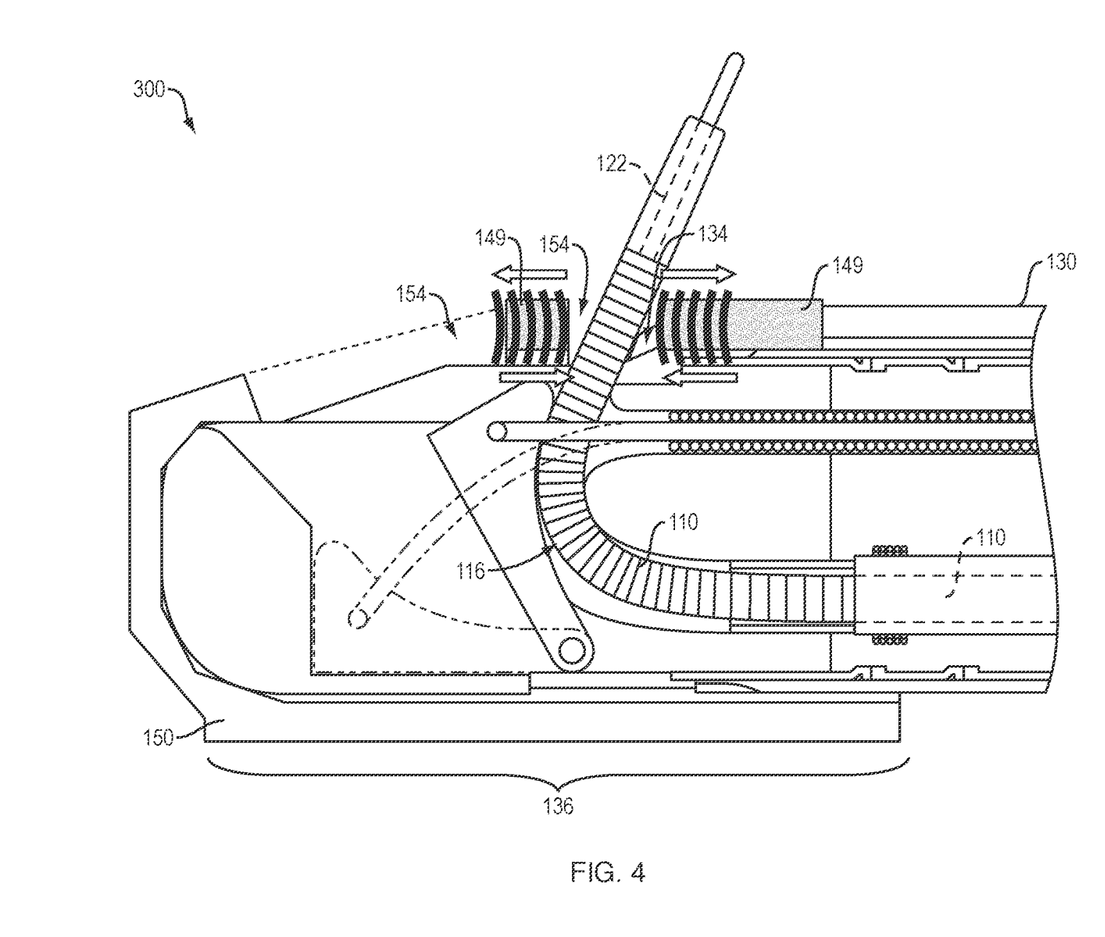
FIG. 4 provides a perspective side view of a medical device and endoscopic accessory tool, according to one embodiment of the present disclosure.

Referring to FIG. 4, in one embodiment, a medical device 300 of the present disclosure may include the identical, or similar, configurations and elements as the medical device 200, with the exception that the actuators 149 are positioned within an endcap 150 (e.g., endoscopic accessory cap) disposed around an outer surface of the distal portion 136 of the elongate tubular body 130. The endcap 150 may include an opening 154 configured to align with the opening 134 within the distal portion 136 of the elongate tubular body 130. In various embodiments, an inner dimension of the opening 154 may be sufficiently large to prevent blocking, occluding or otherwise impairing the function of any accessories, tools, ports, channels or electronics (e.g., light source, camera, etc.) on, within or extending through the distal portion 136 of the elongate tubular body 130. In one embodiment, the endcap 150 may comprise a variety of polymeric, hard plastic, soft plastic, rubber and/or neoprene materials with an atraumatic outer dimension configured to navigate through tortuous, narrow or otherwise restricted body passageways. The endcap 150 may be permanently attached to the distal portion 136 of the elongate tubular body 130 by a suitable weld, solder, braze, adhesive, epoxy, glue and/or resin. In addition, or alternatively, the endcap 150 may be reversibly attached to the distal portion 136 of the elongate tubular body 130 by at least one of a snap-fit, press-fit, interference fit, compressive fit, static friction fit, thread and collar fit, lock-and-key fit, luer-lock, and the like.

One or more actuators 149 may be disposed on or within the endcap 150 around or adjacent to the opening 154. As above, the actuators(s) 149 may be arranged in a variety of numbers, locations, arrangements and/or orientations configured to transmit mechanical motion to the distal portion 116 of the elongate member 110 and guidewire 122 extending through the opening 154 in the x, y and/or z directions, e.g., along, across or above the plane of the medical device 300. In various embodiments, mechanical motion transmitted to a distal portion 116 of the elongate member 110 extending above the plane of the outer surface of the medical device 300, e.g., closer to the distal end of the elongate member 110 and guidewire 122, may provide the medical professional with enhanced control of the endoscopic accessory tool and guidewire when attempting to access the major papilla, steer towards a target duct and/or navigate beyond strictures, obstructions and the like.

Although the medical devices 200, 300 of the present disclosure include one or more actuators configured to transmit mechanical motion to the distal tip of an elongate member 110 and guidewire 122 of an endoscopic accessory tool 100, in various embodiments of the present disclosure, one or more actuators may be disposed on or within the endoscopic accessory tool itself.

Figure 5A:
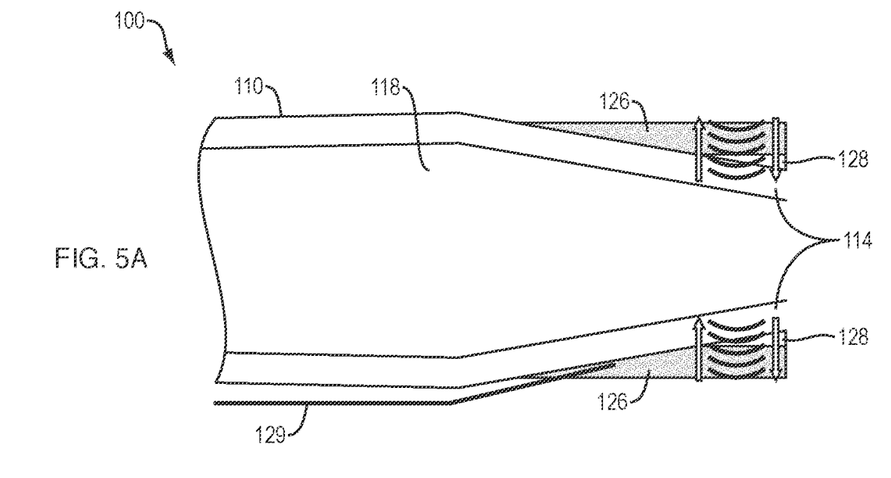
FIGS. 5A-5D provide perspective side (FIGS. 5A and 5C) and front (FIGS. 5B and 5D) views of a distal portion of an endoscopic accessory tool, according to one embodiment of the present disclosure.
Figure 5B:
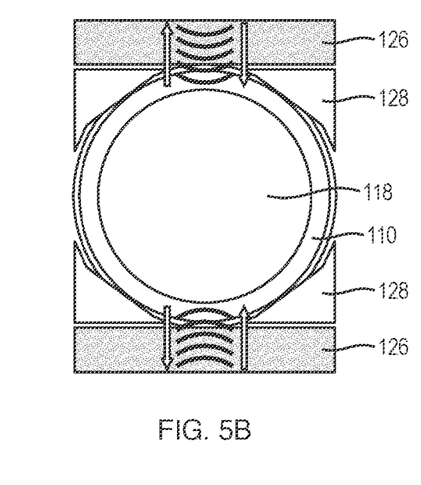
Figure 5C:
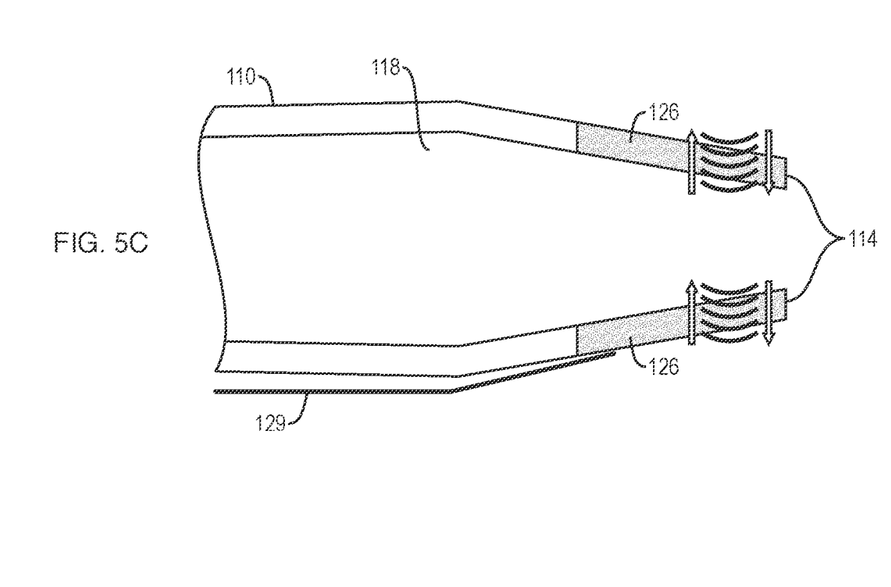
Figure 5D:
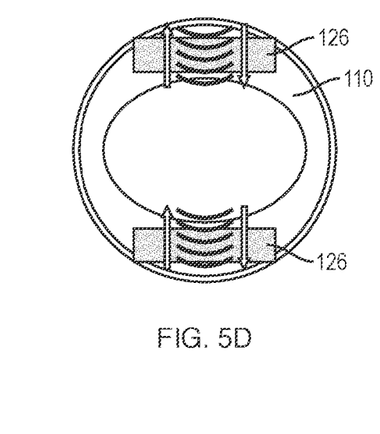

Referring to FIGS. 5A-5B, in one embodiment, an endoscopic accessory tool 100 of the present disclosure, e.g., as disclosed in FIGS. 2A-2C, may further include one or more actuators 126 attached to an outer surface of the elongate member 110 at or near the distal end 114 by a support or attachment member 128. In various embodiments, positioning the actuator(s) 126 on the outer surface of the elongate member 110 may prevent the lumen 118 from being narrowed or otherwise occluded. Referring to FIGS. 5C-5D, in another embodiment, the endoscopic accessory tool 100 may further include one or more actuators 126 embedded or integrated within a wall at or near the distal end 114 of the elongate member 110. In any of the embodiments depicted in FIGS. 5A-5D, the actuator(s) 126 may be connected to a power supply (not shown) by an electrically conductive wire 129 extending along, or embedded within, an inner or outer surface along a length of the elongate member 110. In various embodiments, the wire 129 may be attached to the actuators 126 using a suitable biocompatible adhesive, glue, resin or shrink wrap material, etc. In addition, or alternatively, an entire length or intermittent portions of the conductive wire 129 may be attached to an inner or outer surface of the elongate member 110 as discussed above. Although FIGS. 5A-5D depict two actuators 126 disposed on opposite sides of the distal end 114 of the elongate member 110, in various embodiments, the number, location, arrangement, orientation and/or size of actuators 126 may vary. For example, the actuators 126 may be arranged in an asymmetric pattern to urge or bias the distal portion 116 of the elongate member 110 and guidewire (not shown) to vibrate and move in a particular direction. In addition, or alternatively, opposing actuators 126 with different amplitudes of vibration may be configured to urge or bias the distal portion 116 of the elongate member 110 and guidewire (not shown) to vibrate and move in a particular direction, e.g., vibration is biased in the direction of the actuator(s) with the greater amplitude of vibration. In various embodiments, the ability to transmit mechanical motion directly within the distal end 114 of the elongate member 110 may provide the medical professional with finer control of the endoscopic accessory tool 100 when accessing the ampullary entry. In addition, or alternatively, the ability to preferentially urge or bias the direction of vibration, as discussed above, may allow the medical professional to more precisely steer with guidewire 122 and elongate member 110 into the CBD or PD, e.g., as the asymmetric vibration is intermittently toggled on/off.

Figure 6A:
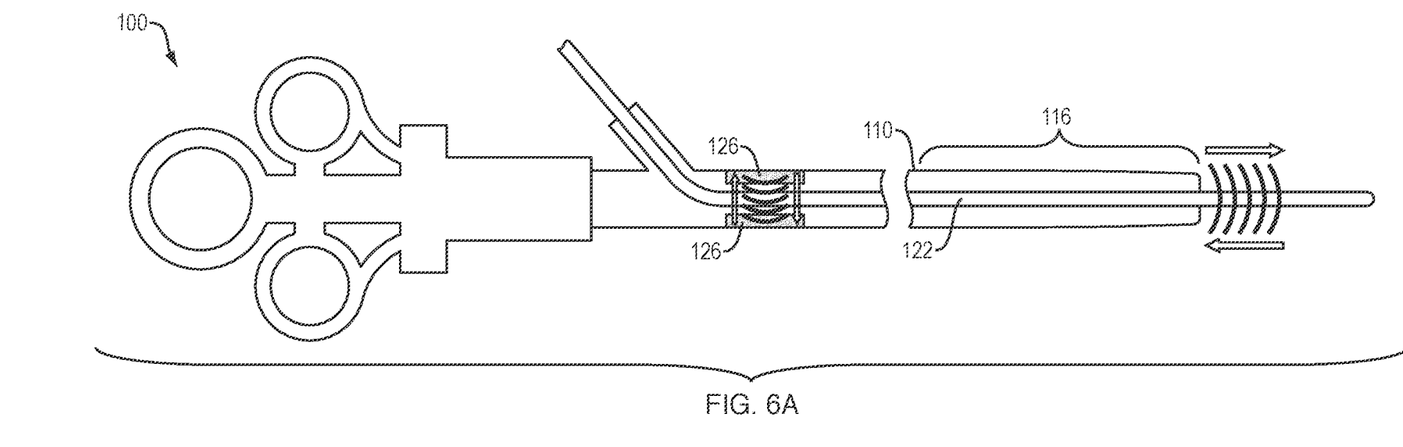
FIGS. 6A-6B provide perspective views of an endoscopic accessory tool, according to one embodiment of the present disclosure.
Figure 6B:
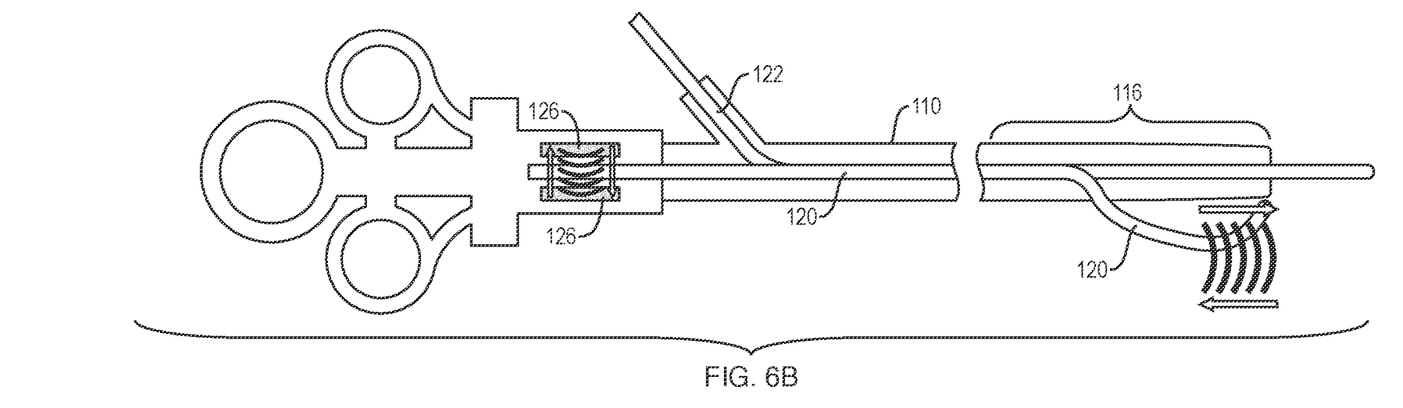

Referring to FIGS. 6A-6B, in one embodiment, an endoscopic accessory tool 100 of the present disclosure, e.g., as disclosed in FIGS. 2A-2C, may further include one or more actuators 126 disposed within a proximal portion of the elongate member 110, e.g., within or near a handle of the endoscopic accessory tool 100, to propagate vibrational energy along a full length of the elongate member 110 and transmit mechanical motion to the distal portion 116 of the elongate member 110 and guidewire 122, as discussed above. Without limiting the present disclosure to specific compositions or compounds, in one embodiment, the endoscopic accessory tool 100 may include a metallic material (e.g., rod, shaft, beam, wire, coil, etc.) which spans the full length of the elongate member 110 (e.g., along an inner our outer surface of the elongate member, or embedded within the wall of the elongate member) to vibrationally connect the actuator(s) 126 to the distal portion 116 of the elongate member 110 and guidewire 122. In various embodiments, mechanical motion transmitted in the −z to +z direction within the proximal portion of the elongate member 110 may urge the distal portion 124 of the guidewire 122 to move linearly in the −x to +x direction. In one embodiment, in addition to propagating vibrational energy along the full length of the elongate member 110, the actuators(s) 126 may be configured to transmit mechanical motion directly onto, and along a length of, the guidewire 122 (FIG. 6A) and/or the cutting wire 120 (FIG. 6B) extending along or through the elongate member 110.

The actuators 149, 126 of any of the medical devices 200, 300 or endoscopic accessory tools 100 of the present disclosure may include acoustic, electromechanical and/or piezoelectric elements, as are commonly known in the art, to transmit mechanical motion to a distal portion of the endoscopic accessory tool. Electrical power may be delivered to these acoustic, electromechanical and/or piezoelectric elements using, by way of non-limiting example, batteries (e.g., external to or as a component of the medical device or endoscopic accessory tool), wires or other electrically conductive circuits or materials extending along or through a length of the medical device or endoscopic accessory tool, or plug-and-play adaptors integrated with a serial port (e.g., Bluetooth, RFID chips, sensors, etc.) located on or within a distal portion of the medical device or endoscopic accessory tool. Using a step pedal, push button, joystick, touch screen, voice command, and the like, the medical professional may transfer power (e.g., toggle on/off, increase or decrease the amplitude and/or direction of vibration) to any or all of the actuators on demand with real-time control while imaging the target passageway, e.g., through an endoscopic camera or using external fluoroscopic or radiologic guidance.

Figure 7A:
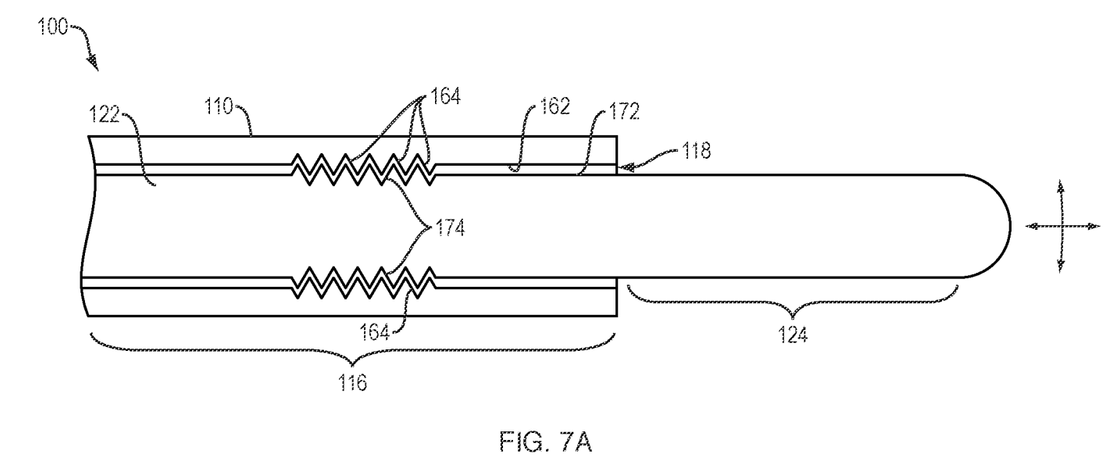
FIGS. 7A-7D provide perspective views of an endoscopic accessory tool and guidewire, according to one embodiment of the present disclosure.
Figure 7B:
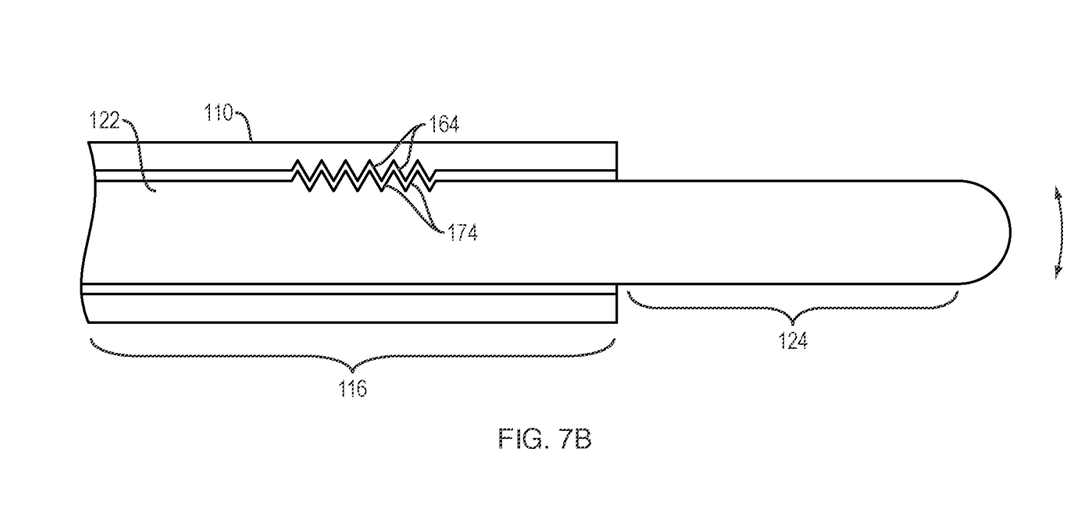
Figure 7C:
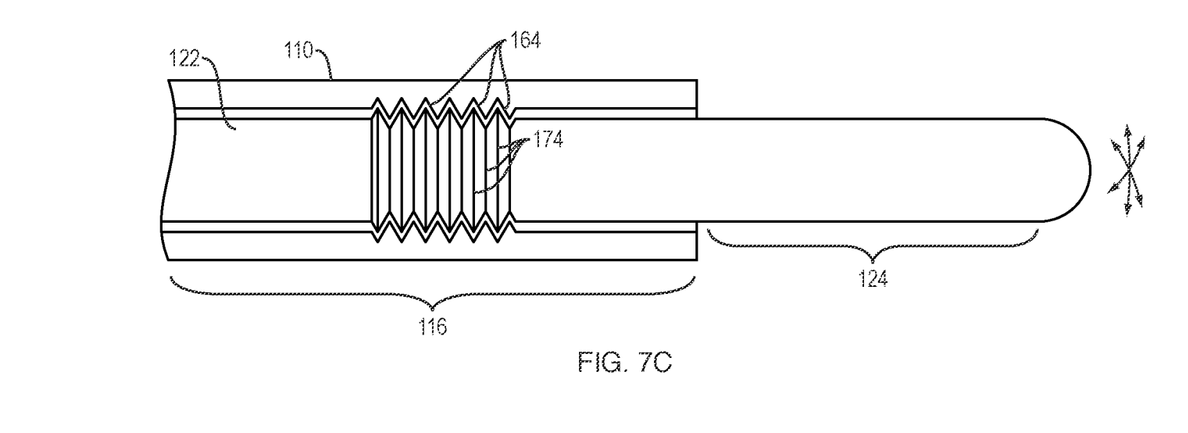
Figure 7D:
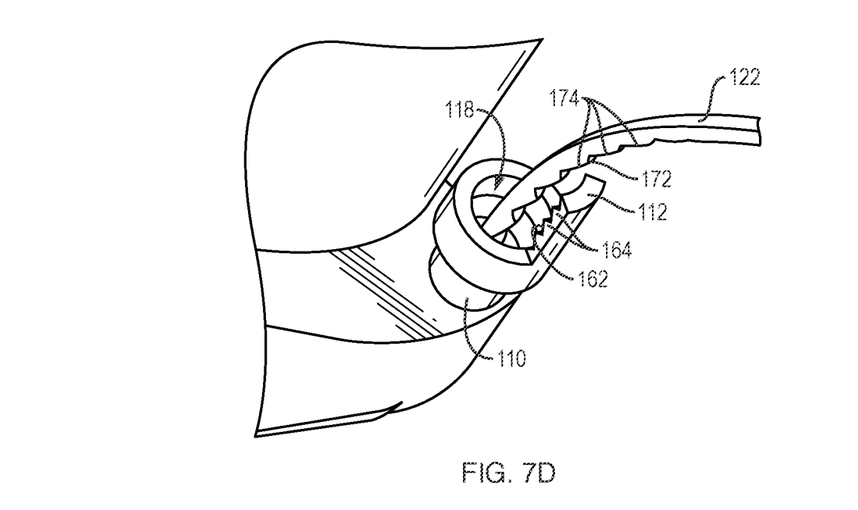

Endoscopic accessory tools of the present disclosure are not limited to the embodiments of FIGS. 5A-5D and 6A-6B, e.g., which may utilize acoustic, electromechanical and/or piezoelectric actuators to transmit mechanical motion to the distal portion 116 of the elongate member 110. Referring to FIGS. 7A-7D, in various embodiments, an endoscopic accessory tool 100 of the present disclosure may include an elongate member 110 and guidewire 122 with corresponding surface features configured to transmit mechanical motion to the distal portion 116 of the elongate member 110 and, by proxy the guidewire 122 itself, as the surface features move relative to each other. Referring to FIG. 7A, in one embodiment, an inner surface 162 of the distal portion 116 of the elongate member 110 may include a series of surface features 164 (e.g., gear-rack, grooves, etc.) configured to mate with a corresponding series of surface features 174 (e.g., ratchet, teeth, etc.) on an outer surface 172 of a distal portion 124 of the guidewire 122. As the elongate member 110 and guidewire 122 move relative to each other, e.g., by proximally retracting and distally advancing the guidewire 122 within the lumen 118 of the elongate member 110 (e.g., back-and-forth in the −x to +x direction), the surface features 164, 174 may move across each other to transmit mechanical motion to the distal portions 116, 124 of the elongate member 110 and guidewire 122. Referring to FIG. 7B, in one embodiment, the surface features 164, 174 may be disposed on one side of the elongate member 110 and guidewire 122 to transmit unidirectional mechanical motion to the distal portions 116, 124 of the elongate member 110 and guidewire 122. Alternatively, referring to FIG. 7C, in one embodiment, the surface features 164, 174 may be disposed around an entire circumference of the elongate member 110 and guidewire 122 to transmit random or multi-directional mechanical motion to the distal portions 116, 124 of the elongate member 110 and guidewire 122. Referring to FIG. 7D, in one embodiment, an inner surface 162 of the proximal end 112 of the elongate member 110 may include a series of surface features 164 configured to mate with a corresponding series of surface features 174 on an outer surface 172 of a proximal end of the guidewire 122. As the elongate member 110 and guidewire 122 move relative to each other, e.g., by proximally retracting and distally advancing the guidewire 122 within the lumen 118 of the elongate member 110 (e.g., back-and-forth in the −x to +x direction), the surface features 164, 174 may move across each other to propagate vibrational energy along a full length of the elongate member 110 and guidewire 122 to transmit mechanical motion to the distal portion 116 of the elongate member 110 and guidewire 122, as discussed above. In various embodiments, the medical professional may move the elongate member 110 and guidewire relative to each other using, e.g., a push-mechanism or roller mechanism mounted within a handle of the endoscopic accessory tool 100.

Figure 8A:
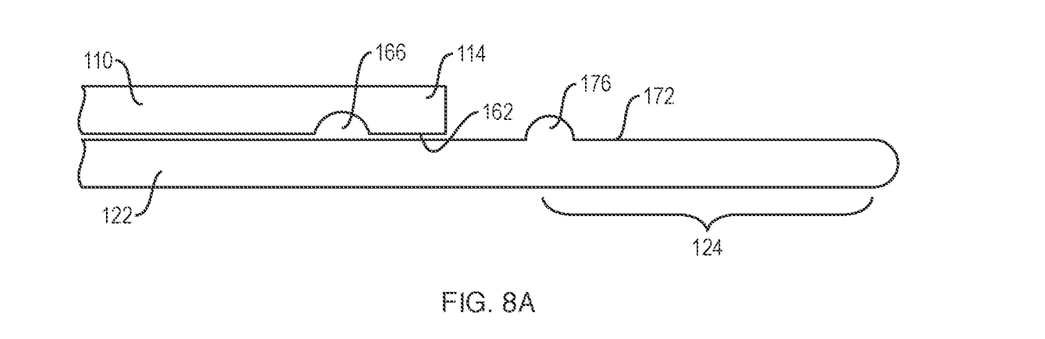
FIGS. 8A-8D provide perspective views of an endoscopic accessory tool and guidewire, according to one embodiment of the present disclosure.
Figure 8B:
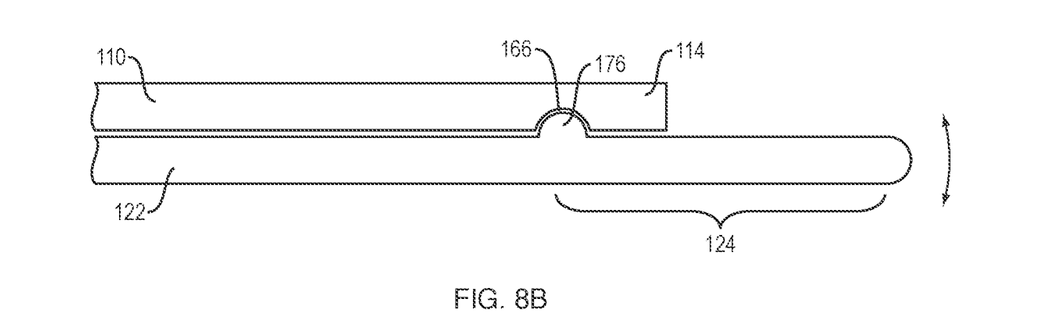
Figure 8C:
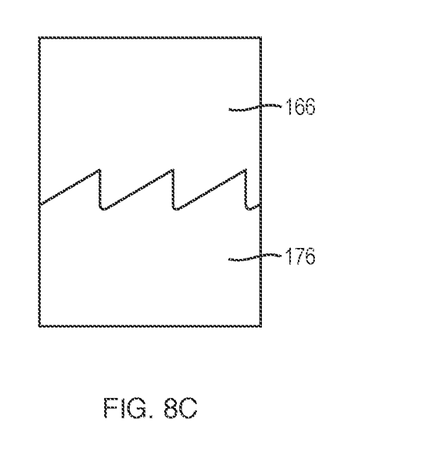
Figure 8D:
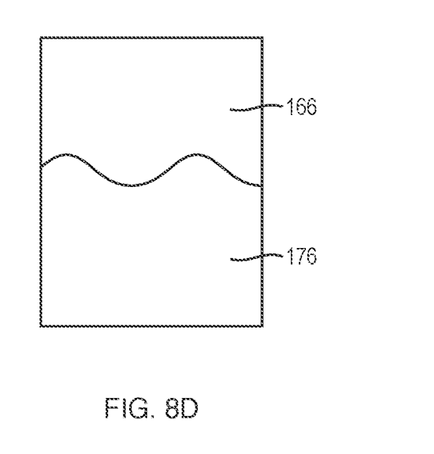

Referring to FIGS. 8A-8D, in various embodiments, an endoscopic accessory tool 100 of the present disclosure may include an elongate member 110 and guidewire 122 with corresponding surface features configured to transmit mechanical motion to a full length of the guidewire 122 as the elongate member 110 is rotated, e.g., an alternating side-to-side or circular/spinning direction. Referring to FIG. 8A, in one embodiment, an inner surface 162 of the distal portion 116 of the elongate member 110 may include a surface feature 166 (e.g., notch, slot, etc.) configured to mate with a corresponding surface feature 176 (e.g., bump, protrusion, etc.) on an outer surface 172 of a distal portion 124 of the guidewire 122. With the surface features 166, 176 of the elongate member 110 and guidewire 122 engaged (FIG. 8B), a proximal end of the elongate member 110 may be rotated as describe above to impart corresponding rotation along a full length of the guidewire 122. In various embodiments, a distal portion 124 of the guidewire 122 extending distally beyond the distal end 114 of the elongate member 110 may bend, flop, twist and/or rotate in a variety of directions as the interlocked elongate member 110 and guidewire 122 are rotated. In various embodiments, the interlocking surface features are not limited to the notch and protrusion configuration described above, but may include corresponding teeth and groove configurations (FIG. 8C) or corresponding sinusoidal or wave-form configurations (FIG. 8D).

The medical devices of the present disclosure are not limited to duodenoscopes, and may include a variety of medical devices for accessing body passageways, including, for example, catheters, ureteroscopes, bronchoscopes, colonoscopes, arthroscopes, cystoscopes, hysteroscopes, and the like.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
    an elongate tubular body having a proximal end, a distal end, and a length therebetween, the elongate tubular body including a first lumen, wherein a distal portion of the elongate tubular body includes an opening in communication with the first lumen;
    an elevator disposed at a first location within the distal portion of the elongate tubular body, wherein the elevator is configured to move between a first position and a second position relative to a longitudinal axis of the elongate tubular body; and
    an actuator disposed at a second location within the distal portion of the elongate tubular body.

2. The medical device of claim 1, wherein the second location is adjacent to the first location such that the actuator is configured to transmit mechanical motion to the elevator.

3. The medical device of claim 2, wherein the actuator is mounted adjacent to a surface of the elevator.

4. The medical device of claim 2, wherein the actuator is in direct contact with the elevator.

5. The medical device of claim 2, wherein the actuator is embedded on or within a portion of the elevator.

6. The medical device of claim 1, wherein the second location is on one side of the first lumen proximal to the elevator.

7. The medical device of claim 1, wherein the second location is on opposite sides of the first lumen proximal to the elevator.

8. The medical device of claim 1, wherein the elongate tubular body further includes a second lumen adjacent to first lumen.

9. The medical device of claim 1, wherein the first lumen is configured to receive an endoscopic accessory tool therethrough, and wherein the elevator is configured to act upon a distal portion of the endoscopic accessory tool as the elevator moves between the first and second positions.

10. The medical device of claim 9, wherein the actuator is configured to transfer mechanical motion to the distal portion of the endoscopic accessory tool.

11. The medical device of claim 1, wherein the elevator comprises a ramp.

12. The medical device of claim 11, wherein the first position is a lowered position and the second position is a raised position in which the ramp is angled relative to the longitudinal axis of the elongate tubular body.

13. The medical device of claim 1, wherein the opening is a side opening.

14. The medical device of claim 13, wherein the elevator comprises a ramp and wherein the ramp is located at a third location within the distal portion of the elongate tubular body at a junction of the side opening and the first lumen.

15. The medical device of claim 13, wherein the first lumen is configured to slidably receive an endoscopic accessory tool therethrough, and wherein the elevator is configured to act upon a distal portion of the endoscopic accessory tool and direct the distal portion of the endoscopic accessory tool to the side opening.

16. The medical device of claim 15, wherein the actuator is configured transmit mechanical motion to the distal portion of the endoscopic accessory tool adjacent the side opening.

17. The medical device of claim 16, wherein the second location is on one side of the endoscopic accessory tool proximal to the elevator when the endoscopic accessory tool is received in the first lumen, or wherein the second location is on opposite sides of the endoscopic accessory tool proximal to the elevator when the endoscopic accessory tool is received in the first lumen.

18. The medical device of claim 1, further comprising an elevator wire that extends along a length of the elongate tubular body, wherein a distal end of the elevator wire is attached to the elevator such that proximally retracting the elevator wire moves the elevator from the first position to the second position and distally advancing the elevator wire moves the elevator from the second position to the first position.

* * * * *